(12) United States Patent
Klimko et al.

(10) Patent No.: US 7,687,539 B1
(45) Date of Patent: *Mar. 30, 2010

(54) METHOD OF TREATING OCULAR ALLERGY

(75) Inventors: Peter G. Klimko, Fort Worth, TX (US); Clay Beauregard, Burleson, TX (US)

(73) Assignee: Alcon Research, Ltd., Fort Worth, TX (US)

(*) Notice: Subject to any disclaimer, the term of this patent is extended or adjusted under 35 U.S.C. 154(b) by 731 days.

This patent is subject to a terminal disclaimer.

(21) Appl. No.: 11/593,714

(22) Filed: Nov. 7, 2006

Related U.S. Application Data

(60) Provisional application No. 60/734,194, filed on Nov. 7, 2005.

(51) Int. Cl.
*A61K 31/366* (2006.01)
*A61K 31/20* (2006.01)

(52) U.S. Cl. .................. 514/460; 514/546; 514/558

(58) Field of Classification Search ............... 424/427, 424/451; 514/460, 463, 546, 558
See application file for complete search history.

(56) References Cited

U.S. PATENT DOCUMENTS

| 5,079,261 | A  | 1/1992  | Serhan et al. ............... 514/552 |
| 6,645,978 | B1 | 11/2003 | Gamache et al. ............ 514/310 |
| 2006/0058375 | A1 | 3/2006 | Klimko et al. .............. 514/460 |
| 2006/0099248 | A1 | 5/2006 | Klimko et al. .............. 424/451 |

FOREIGN PATENT DOCUMENTS

| WO | WO 03/039533 A1 | 5/2003 |
| WO | WO 03/040080 A3 | 5/2003 |

OTHER PUBLICATIONS

Bielory et al., "Efficacy and Tolerability of Newer Antihistmines in the Treatment of Allergic Conjunctivitis," *Drugs*, vol. 65(2), pp. 215-228 (2005).
Bonnans et al., "Lipoxins in astham: potential therapeutic mediators on bronchial inflammation?", *Allergy*, vol. 59 (10), pp. 1027-1041 (2004).
Chiang et al., "Activation of Lipoxin $A_4$ Receptors by Aspirin-triggered Lipoxins and Select Peptides Evokes Ligand-specific Responses in Inflammation," *J. Exp. Med.*, vol. 191 (7), pp. 1197-1207 (2000).
Fiore et al., "Identification of a Human cDNA Encoding a Funcitonal High Affinity Lipoxin $A_4$ Receptor," *J. Exp. Medicine*, vol. 180, pp. 253-260 (1994).
Fiorucci et al., "A β-oxidation-resistant lipoxin $A_4$ analog treats hapten-induced colitis by attenuating inflammation and immune dysfunction," *Proc. Nat. Acad. Sci.*. vol. 101(44), pp. 15736-15741 (2004).
Gavins et al., "Leukocyte antiadhesive actions of annexin 1: ALXR- and FPR-related antiflammatory mechanisms," *Blood*, vol. 101 (10), pp. 4140-4147 (2003).
Gilroy et al., "Inflammatory Resolution: New Opportunities for Drug Discovery," *Nature Reviews*, vol. 3, pp. 401-416 (2004).
Gronert et al., "Selectivity of Recombinant Human Leukotriene $D_4$, Leukotriene $B_4$, and Lipoxin $A_4$ Receptors with Aspirin-Triggered 15-epi-$LXA_4$ and Regulation of Vascular and Inflammatory Responses," *American J. of Pathology*, vol. 158 (1), pp. 3-9 (2001).
Guilford et al., Novel 3-Oxa Lipoxin $A_4$ Analogues with Enhanced Chemical and Metabolis Stability Have Anti-inflammatory Activity in Vivo, *J. Med. Chem.*, vol. 47, pp. 2157-2165 (2004).
József et al., "Lipoxin $A_4$ and aspirin-triggered 15-epi-lipoxin $A_4$ inhibit peroxynitrite formation, NF-κB and AP-1 activation, and IL-8 gene expression in human leukocytes," *Proc. Nat. Acad. Sci.*, vol. 99(20), pp. 13266-13271 (2002).
Karp et al., "Defective lipoxin-mediated anti-inflammatory activity in the cystic fibrosis airway," *Nature Immun.*, vol. 5(4), pp. 388-392, (2004).
Le et al., "Pleiotropic roles of formyl peptide receptors," *Cytokine Growth Factor Reviews*, vol. 12, pp. 91-105 (2001).
Lee et al., "Inhibition of Leukotriene $B_4$-Induced Neutrophil Migration by Lipoxin $A_4$: Structure-Function Relationships," *Biochemical and Biophysical Research Communications*, vol. 180 (3), pp. 1416-1421 (1991).
Levy et al., "Multi-pronged inhibition of airway hyper-responsiveness and inflammation by lipoxin $A_4$", *Nature Medicine*, vol. 8(9), pp. 1018-1023 (2002).
Lin et al., "Modulation of $LTB_4$ Receptor in T-Lymphocytes by Lipoxin $A_4$ ($LXA_4$) and its Role in Delayed-Type Hypersensitivity;" *Advances in Exp. Medicine and Biology*, vol. 447, pp. 151-163 (1999).
Melo et al., "Cutting Edge: Lipoxin (LX) $A_4$ and Aspirin—Triggered 15-Epi-$LXA_4$ Block Allergen-Induced Eosiniophil Trafficking," *J. of Immunology*, vol. 164, pp. 2267-2271 (2000).
Ono et al., "Allergic conjunctivitis: Update on pathophysiology and prospects for future treatment," *J. Allergy Clin. Immunology*, vol. 115 (1), pp. 118-122 (2005).
Parente et al., "Annexin 1: More than an anti-phospholipase protein," *Inflammation Res.*, vol. 53, pp. 125-132 (2004).
Perretti et al., "Endogenous lipid- and peptide-derived anti-inflammatory pathways generated with glucocorticoid and aspirin treatment activate the lipoxin $A_4$ receptor," *Nature Medicine*, vol. 8(11), pp. 1296-1302 (2002).
Petasis et al., "Design, synthesis and bioactions of novel stable mimetics of lipoxins and aspirin-triggered lipoxins," *Prostaglandins, Leukotrienes and Essential Fatty Acids*, vol. 72, pp. 201-321 (2005).
Schottelius et al., "An Aspirin-Triggered Lipoxin $A_4$ Stable Analog Displays a Unique Topical Anti-Inflammatory Profile," *J. of Immunology*, vol. 169, pp. 7063-7070 (2002).
Vachier et al., "Severe asthma is associated with a loss of LX4, an endogenous anti-inflammatory compound," *J. Allergy Clin Immunology*, vol. 115(1), pp. 55-60 (2005).

*Primary Examiner*—Michael G Hartley
*Assistant Examiner*—Jagadishwar R Samala
(74) *Attorney, Agent, or Firm*—Patrick M. Ryan

(57) ABSTRACT

The topical use of 5,6,7-trihydroxyheptanoic acid and analogs alone or in combination with histamine antagonists and/or mast cell stabilizers is disclosed for the treatment of ocular allergy.

11 Claims, No Drawings

METHOD OF TREATING OCULAR ALLERGY

This application claims priority to U.S. Provisional Application, U.S. Ser. No. 60/734,194 filed Nov. 7, 2005.

The present invention is directed to the topical treatment of ocular allergic disorders, such as allergic conjunctivitis, giant papillary conjunctivitis, vernal conjunctivitis, and atopic keratoconjunctivitis. In particular, the present invention is directed toward the topical use of 5,6,7-trihydroxyheptanoic acid and its analogs to treat ocular allergy.

BACKGROUND OF THE INVENTION

The eye, particularly the conjunctiva, has a relatively large number of mast cells. When allergens are present they can bind to immunoglobulins on the surface of these mast cells and trigger their degranulation (breakdown). Degranulation releases mast cell components, including histamine, into the environment outside the mast cell. Through a variety of mechanisms these components produce ocular surface inflammation resulting in itching, tearing, lid and conjunctival edema/redness, and photophobia. This is frequently designated as an acute phase response, as is seen with seasonal allergic conjunctivitis and perennial allergic conjunctivitis. Topical ocular application of histamine receptor antagonists such as olopatidine or mast cell stabilizers such as lodoxamide are frequently used to alleviate these symptoms [for a review, see: Bielory et al., *Drugs* 2005, 65(2), 215-228].

As is the case in other allergic diseases, the acute phase response can progress to a late phase response characterized by an influx of eosinophils and neutrophils into the conjunctiva. In the associated chronic allergic disease, exemplified by vernal keratoconjunctivitis, atopic keratoconjunctivitis, and giant papillary conjunctivitis, eyelid swelling and remodeling of the ocular surface tissues can occur. In severe cases the patient experiences extreme discomfort and sustains damage to the ocular surface. For such instances there is no highly effective and safe treatment regimen. Although topical administration of corticosteroids is effective in severe cases, chronic use is contraindicated due to an increased risk for the development of cataracts and glaucoma [for a review, see: Ono and Abelson, *J. Allergy Clin. Immunol.* 2005, 115(1), 118-122].

Lipoxin $A_4$ is an anti-inflammatory eicosanoid biosynthesized from arachidonic acid, and is produced locally at inflammation sites via the interaction of neutrophils with platelets or of other leukocytes with epithelial cells. Lipoxin $A_4$ is believed to act endogenously to resolve inflammation by inducing apoptosis and phagocytosis/clearance of activated leukocytes. Lipoxin $A_4$ binds to at least two receptors with nM affinity. The first is the lipoxin $A_4$ cognate receptor, called ALXR. This is the same as the formyl peptide receptor FPRL-1. The second receptor is that for the cysteinyl leukotriene $LTD_4$. Lipoxins are thought to function as ALXR agonists and $LTD_4$ receptor antagonists [Fronert et al., *Am. J. Pathol.* 2001, 158(1), 3-8].

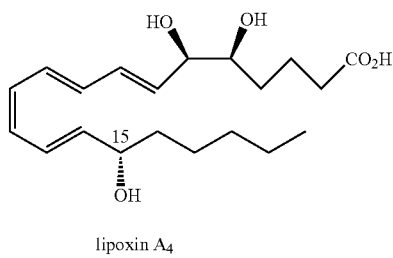

lipoxin $A_4$

Several researchers have reported that administration of lipoxin $A_4$ structural analogs inhibit allergen-induced eosinophil infiltration, decrease production of pro-inflammatory allergic mediators like cysteinyl leukotrienes, IL-5, and eotaxin, and reduce tissue edema in several animal models, including: a mouse model of allergic asthma [Levy et al., *Nat. Med.* 2002, 8(9), 1018-1023]; allergen-induced skin inflammation in mice and guinea pigs [Schottelieus et al., *J. Immun.* 2002, 169, 7063-7070]; and allergen-induced pleurisy in rats [Bandeira-Melo et al., *J. Immun.* 2000, 164(5), 2267-2271].

Lee et al. have disclosed that compounds 1 and 2 inhibit $LTB_4$-induced chemotaxis of neutrophils as potently as lipoxin $A_4$ [Lee et al., *Biochemical and Biophysical Research Communications* 1991, 180(3), 1416-21]. As the authors' stated purpose was to investigate the relationship between this bioassay readout and the structure of lipoxin $A_4$ analogs that they synthesized, one conclusion could be that compounds 1, 2, and lipoxin $A_4$ inhibit $LTB_4$-induced neutrophil chemotaxis by the same mechanism, namely activation of the ALXR.

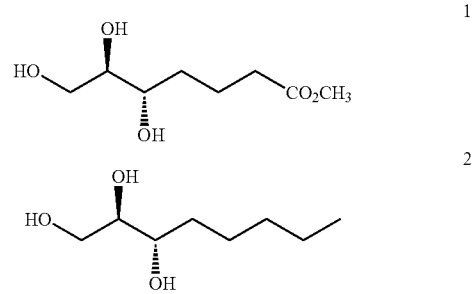

However, this theory may well be invalid. An essential experiment to test this theory would be to ascertain whether the chemotaxis inhibition effect for these three compounds could be blocked by a selective ALXR antibody or small molecule antagonist. This was not performed, since at the time of Lee et al.'s disclosure neither the ALXR protein nor its associated mRNA had been sequenced [this was accomplished in 1994: *J. Exp. Med.* 1994, 180(1), 253-260]. An explanation for the neutrophil chemotaxis inhibition displayed by 1, 2, and lipoxin $A_4$ which is equally consistent with this disclosure would be that 1 and 2 act via leukotriene $B_4$ receptor antagonism while lipoxin $A_4$ acts via ALXR agonism and/or perhaps antagonism at the leukotriene $D_4$ ($LTD_4$) receptor [Gronert et al., *Am. J. Path.* 2000, 158(1), 3-9]. Furthermore it is known that the biological activity of lipoxin $A_4$ is critically dependent on the presence of a hydroxyl at position 15; oxidation to the carbonyl [Petasis et al., *Prostaglandins Leukot. Essent Fatty Acids* 2005, 73(3-4), 301-321] or replacement with a hydrogen [Jozsef et al., *Proc. Natl. Acad. Sci. USA* 2002, 99(20), 13266-13271] greatly diminishes biological activity. However 1 and 2 lack this hydroxyl, indeed they lack any atoms at all beyond the primary hydroxyl group of their triol array. To the best of our knowledge there have been no subsequent reports on the biological activities of either 1 or 2. Thus absent receptor-linked functional data, one skilled in the art could reasonably doubt that these compounds' inhibition of $LTB_4$-induced neutrophil chemotaxis is due to ALXR agonism.

SUMMARY OF THE INVENTION

The present invention is directed to methods for the topical treatment of ocular allergy, including seasonal and perennial allergic conjunctivitis, vernal keratoconjunctivitis, atopic keratoconjunctivitis, and giant papillary conjunctivitis.

According to the methods of the present invention, a 5,6,7-trihydroxyheptanoic acid or analog is topically administered to a patient, alone or in combination with a histamine receptor antagonist and/or a mast cell degranulation inhibitor, such as olopatidine and emedastine. The 5,6,7-trihydroxyheptanoic acid or analog is administered in an ophthalmic composition dosed topically to a patient's eye.

DETAILED DESCRIPTION OF THE INVENTION

Unless indicated otherwise, all component amounts are presented on a % (w/v) basis.

According to the methods of the present invention, a composition comprising a compound of formula I alone or in combination with a histamine receptor antagonist and/or a mast cell degranulation inhibitor is topically administered to a mammal in need thereof:

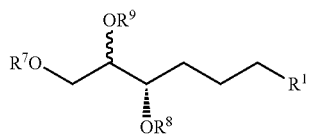

I wherein
$R^1$ is $C_2H_5$, $CO_2R$, $CONR^2R^3$, $CH_2OR^4$, or $CH_2NR^5R^6$, where:
  R is H, $C_{1-6}$ straight chain or branched alkyl, $C_{3-6}$ cycloalkyl, or phenyl, or $R^1$ is a carboxylate salt of formula $CO_2^-R^+$, where $R^+$ is $Li^+$, $Na^+$, $K^+$, or an ammonium moiety of formula $^+NR^{10}R^{11}R^{12}R^{13}$;
  $R^2$, $R^3$ are independently H, $C_{1-6}$ alkyl, $C_{3-6}$ cycloalkyl, benzyl, phenyl, OH, $OCH_3$, or $OC_2H_5$, provided that at most only one of $R^2$, $R^3$ is OH, $OCH_3$, or $OC_2H_5$;
  $R^4$ is H, $C(O)R^{14}$, $C_{1-6}$ alkyl, $C_{3-6}$ cycloalkyl, benzyl, or phenyl;
  $R^5$, $R^6$ are independently H, $C(O)R^{14}$, $C_{1-6}$ alkyl, $C_{3-6}$ cycloalkyl, benzyl, phenyl, OH, $OCH_3$, or $OC_2H_5$, provided that at most only one of $R^2$, $R^3$ is OH, $OCH_3$, or $OC_2H_5$;
  $R^7$, $R^8$, and $R^9$ are independently H, $CH_3$, $C_2H_5$, $C(O)R^{14}$, or $CO_2R^5$;
  or $R^7$ and $R^8$ or $R^8$ and $R^9$ together constitute a carbonyl group (C=O), thus forming a cyclic carbonate;
  or $OR^8R^1$ together form a cyclic ester (a lactone);
  $R^{10}$-$R^{13}$ are independently H or $C_{1-6}$ alkyl, each alkyl group optionally bearing an OH or $OCH_3$ substituent;
  $R^{14}$ is H, $C_{1-6}$ alkyl, $C_{3-6}$ cycloalkyl, benzyl, or phenyl;
  $R^{15}$ is $C_{1-6}$ alkyl, $C_{3-6}$ cycloalkyl, benzyl, or phenyl; and
  ⌇ indicates that the $OR^9$ substituent can be arranged to afford the R or S absolute configuration:

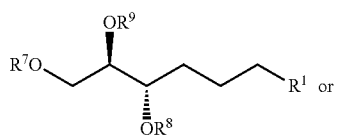

I or

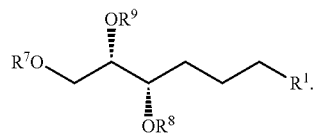

I

Preferred compounds of formula I are those wherein:
$R^1$ is $C_2H_5$, $CO_2R$, $CH_2OR^4$, or a carboxylate salt of formula $CO_2^-R^+$;
$R^+$ is $Li^+$, $Na^+$, $K^+$, or $NH_4^+$;
R is H, $CH_3$, $C_2H_5$, n-$C_3H_7$, or i-$C_3H_7$;
$R^4$ is H, $COCH_3$, or $CH_3$; and
$R^7$, $R^8$, $R^9$ are independently H, $CH_3$, or $CH_3CO$;
or $R^7$ and $R^8$ or $R^8$ and $R^9$ together constitute a carbonyl group (C=O),
thus forming a cyclic carbonate;
or $OR^8R^1$ together form a cyclic ester (a lactone).

Among the especially preferred are compounds 1-6. Compound 1 is commercially available from Biomol Research Laboratories, Plymouth Meeting, Pa., and compound 2 can be prepared as detailed in Lee et. al., *Biochemical and Biophysical Research Communications* 1991, 180(3), 1416-21. Compounds 3-6 can be prepared as described in examples 1-4 below.

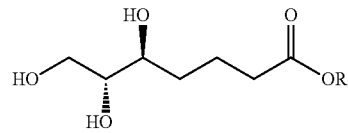

1, R=$CH_3$
4, R-Li
5, R=$C_2H_5$
6, R=i-$C_3H_7$

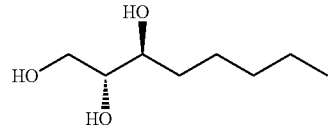

2

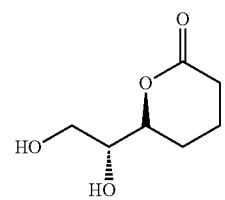

3

Example 1

Synthesis of Compound 3

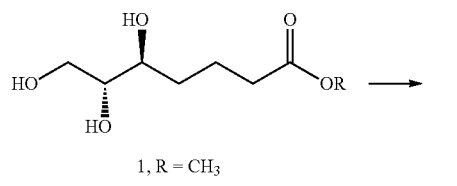

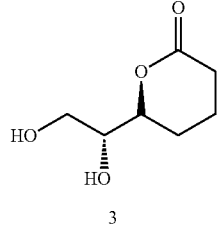

A solution of methyl ester 1 (20 mg, 0.104 mmol) in MeOH (2.1 mL) containing 1 M LiOH (0.5 mL, 0.5 mmol) was heated in a microwave heater at 120° C. for 6 minutes. The reaction was concentrated and the residue was chromatographed on a 10 mm diameter×18 cm tall C18 reverse-phase silica gel column eluting with 7:3 v:v 0.05 M HCl:acetonitrile to afford a crude white solid after concentration (40.9 mg). The solid was rinsed with hot $CH_3CN$ (2×2 mL) and the filtrate was concentrated to afford lactone 3 (7.8 mg, 47%). $^{13}C$ NMR (150 MHz, dmso-$d_6$) δ171.12 (C), 79.86 (CH), 72.44 (CH), 62.03 ($CH_2$), 29.39 ($CH_2$), 21.67 ($CH_2$), 17.55 ($CH_2$).

Example 2

Synthesis of Compound 4

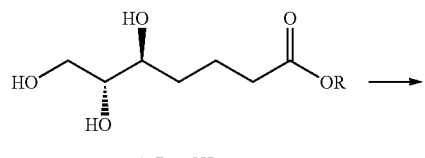

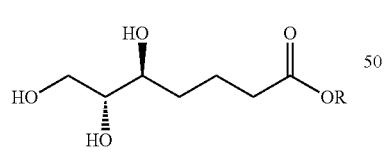

A solution of methyl ester 1 in aqueous MeOH is heated to reflux in the presence of 3 equivalents of lithium hydroxide. After 6 h the reaction is cooled to room temperature and the pH of the solution is adjusted to 6 by the addition of 70-9 mesh sulfonic acid resin MP (commercially available from Novabiochem/EMD Biosciences, 10394 Pacific Center Court, San Diego, Calif. 92121). The solution is filtered through a 0.2 μM poly-terfluoroethylene syringe filter and concentrated to afford the lithium carboxylate 4 as a white solid. $^1H$ NMR ($D_2O$, 400 MHz) δ 3.69-3.64 (m, 1H), 3.55-3.47 (m, 3H), 2.16-2.12 (m, 2H), 1.67-1.64 (m, 1H), 1.54-1.48 (m, 2H), 1.38-1.34 (m, 1H). $^{13}C$ NMR ($D_2O$, 100 MHz) δ183.46 (C), 74.61 (CH), 71.67 (CH), 62.49 ($CH_2$), 37.26 ($CH_2$), 31.55 ($CH_2$), 22.04 ($CH_2$).

Example 3

Synthesis of Compound 8

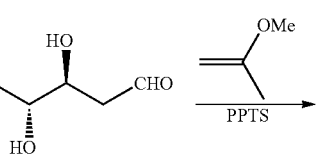

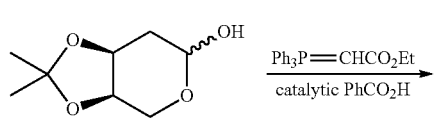

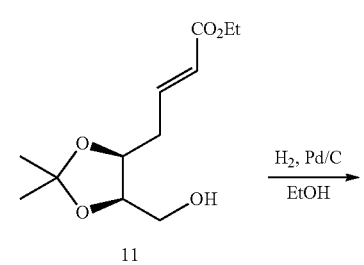

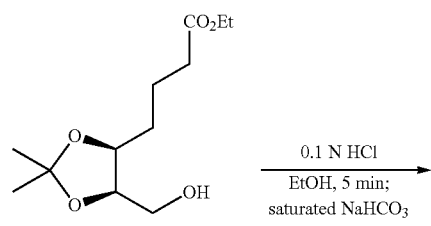

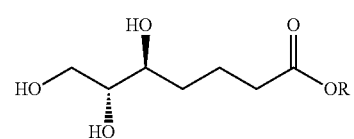

2-deoxy-D-ribose is converted to the acetonide-protected lactol 10 by treatment with 2-methoxypropene and catalytic pyridinium p-toluenesulfonate (PPTS) in ethyl acetate. Wittig reaction with $Ph_3P$=$CHCO_2Et$ in THF in the presence of catalytic benzoic acid affords enoate 11, which is reduced to 12 under a hydrogen atmosphere in the presence of catalytic Pd/C in ethanol. Deprotection of 12 using 0.1 N HCl in ethanol for 5 minutes, followed by quenching with aqueous $NaHCO_3$, affords 8 after silica gel chromatographic purification.

Example 4

Synthesis of Compound 9

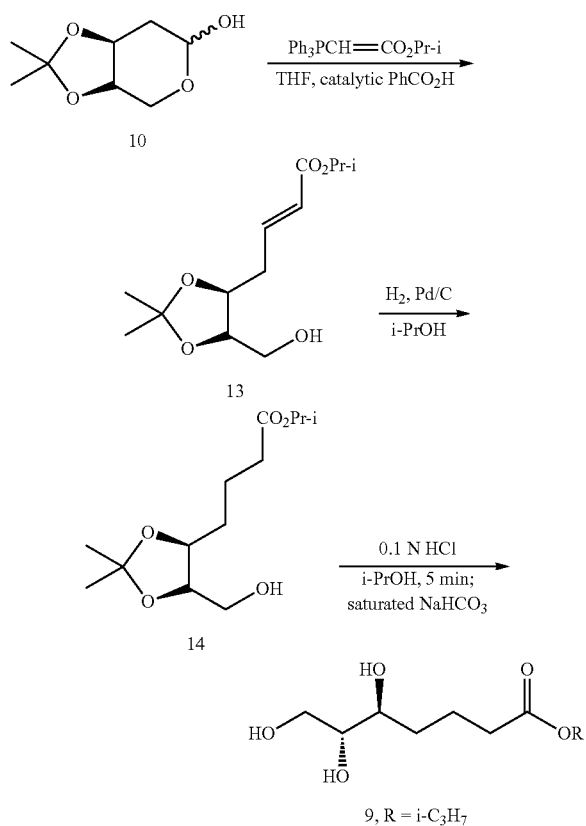

Wittig reaction of lactol 10 with $Ph_3P=CHCO_2Et$ in THF in the presence of catalytic benzoic acid affords enoate 13, which is reduced to 14 under a hydrogen atmosphere in the presence of catalytic Pd/C in isopropanol. Deprotection of 14 using 0.1 N HCl in isopropanol for 5 minutes, followed by quenching with aqueous $NaHCO_3$, affords 9 after silica gel chromatographic purification.

According to the methods of the present invention, a compound of formula I is administered in a pharmaceutically acceptable carrier for topical ophthalmic administration. The compositions are formulated in accordance with methods known in the art. The compositions may contain more than one compound of formula I. Additionally, the compositions may contain a second drug, other than a compound of formula I.

Compound I was evaluated in a mouse model of late-phase allergy as outlined in example 5 below.

Example 5

Activity of Compound 1 in a Mouse Late-Phase Allergy Model

Methods

Active Sensitization and Induction of Allergic Conjunctivitis (AC)

Female BALB/c mice, 6 to 9 months old (Charles River Labs), were given a single intraperitoneal injection of 100 µg chicken ovalbumin (OVA; Sigma) which had been absorbed to 5 mg of alum (Pierce Chemical) as an adjuvant or 5 mg alum only (unsensitized group). On day 14 after sensitization, all mice were challenged with a single topical drop O.D. of 1 mg OVA dissolved in 5 µl PBS.

Drugs or vehicles were administered to mice as a single 5 µl drop O.D. at 60 min before challenge and again at 16 hrs after challenge (BID dosing). Mice were euthanized at 24 hrs after challenge.

EPO Activity Assay

Mice were euthanized at 24 hrs after topical challenge and upper and lower eyelids containing palpebral conjunctiva were excised and immediately frozen on dry ice. Samples were weighed frozen and then thawed and homogenized on ice in 2 ml of 50 mM HEPES buffer, pH 6.5. Samples were pelleted at 4000 rpm for 20 min at 4° C. and supernatants were discarded. To each pellet, 1 ml of 0.5% cetyltrimethylammonium chloride (CTAC) was added and samples were vortexed vigorously. Samples were then subjected to three freeze-thaw cycles between −80° C. and 37° C. After final thaw, samples were sonicated on ice for 15-30 sec and pelleted at 4000 rpm for 20 min at 4° C. EPO activity assay was performed on supernatants.

For the EPO activity assay, 75 µl of each sample were added in triplicate to wells of a 96-well clear flat-bottomed microplate. 75 µl of EPO substrate solution [6 mM o-phenylenediamine (OPD), 8.8 mM $H_2O_2$, and 6 mM KBr in 50 mM HEPES, pH 6.5] were then added to each well using a multichannel pipetter. The reaction was allowed to run for 3 min and was stopped by addition of 150 µl of 4M $H_2SO_4$. Optical density at 490 nm (OD490) was read on a Bio-Tek Synergy HT plate reader. EPO standards were prepared by ½ serial dilutions from 1000 to 15.6 ng/ml of human EPO protein (Calbiochem) in 50 mM HEPES, pH 6.5, with 6 mM KBr. 75 µl triplicates of each standard were used on each run of the assay. Linear regression was determined for the resulting plot of [EPO] vs OD490. Final [EPO] in each sample was determined by solving for x in the equation $y=m*x+b$, where y=OD490, m=x-intercept, and b=slope.

Statistical Methods

Groups of means were compared using Student's unpaired t-test or Dunnett's t-test where appropriate. Means were considered to be significantly different at P<0.05. Data are expressed as mean±standard deviation.

Results

All three doses of 1 tested (0.001%, 0.01%, and 0.1% solutions) significantly inhibited conjunctival EPO activity at 24 hrs post-challenge with comparable efficacy to that of 0.1% dexamethasone (Table 1). Efficacy for each concentration of 1 was comparable 0.1% dexamethasone.

TABLE 1

Conjunctival EPO activity at 24 hrs post-challenge

| Test Item | Dose | EPO Activity (ng/ml/mg tissue) ± S.D.[a] |
|---|---|---|
| —[b] | — | 3.0 ± 0.5 |
| Vehicle | — | 10.5 ± 3.5 |
| dexamethasone | 0.1% | 4.0 ± 0.5[c] |
| compound 1 | 0.001% | 5.2 ± 2.5[c,d] |
| compound 1 | 0.01% | 4.8 ± 1.2[c,d] |
| compound 1 | 0.1% | 3.2 ± 1.0[c,d] |

[a]S.D. = standard deviation. [b]unsensitized mouse. [c]p < 0.05 compared to vehicle-treated group by Dunnet's t-test. [d]Not statistically different from dexamethasone-treated group (p > 0.05 compared to dexamethasone-treated group by Dunnet's t-test).

The compositions of the present invention contain a pharmaceutically effective amount of a compound of formula I.

As used herein, "a pharmaceutically effective amount" means an amount sufficient to reduce or eliminate allergic conjunctivitis symptoms. Generally, the compositions of the present invention will contain from 0.000001 to 1% of a compound of formula I. Preferably, the compositions of the present invention will contain from 0.00003 to 0.01% of a compound of formula I.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 5.5-8.

Topical ophthalmic products are typically packaged in multidose form. Preservatives are typically required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically will not contain a preservative and will be unpreserved.

Generally, 1-2 drops of such compositions will be administered from once to many times per day.

Representative eye drop formulations are provided below in Examples 6 and 7 for treating allergic conjunctivitis.

Example 6

| Ingredient | Concentration (% w/v) |
| --- | --- |
| Compound of formula I | 0.00001 to 1 |
| Ethanol | 0.03-0.2 |
| Boric Acid | 0.1-0.3 |
| Polyoxyl 40 Stearate | 0.1 |
| Edetate Disodium | 0.01 |
| Polyquaternium 1 | 0.001 |
| NaOH/HCl | q.s. to pH 6-8 |
| Purified Water | q.s. to 100% |

Example 7

| Ingredient | Concentration (% w/v) |
| --- | --- |
| Compound of formula I | 0.00003 to 0.01 |
| Hydroxypropyl methylcellulose | 0.1-0.5 |
| Dextran 70 | 0.1 |
| Sodium Chloride | 0.8 |
| Potassium Chloride | 0.12 |
| Dibasic Sodium Phosphate | 0.025 |
| Edetate Disodium | 0.01 |
| Polyquaternium-1 | 0.001-0.005 |
| NaOH/HCl | q.s. to pH 6-8 |
| Purified Water | q.s. to 100 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

We claim:

1. A method for the treatment of ocular allergy in a mammal, which comprises topically administering to the eye of the mammal a composition comprising a pharmaceutically acceptable carrier and a pharmaceutically effective amount of a compound of formula I:

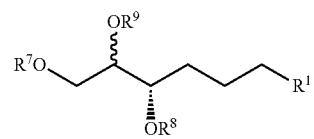

wherein
$R^1$ is $C_2H_5$, $CO_2R$, $CH_2OR^4$, or a carboxylate salt of formula $CO_2^-R^+$;
$R^+$ is $Li^+$, $Na^+$, $K^+$, or $NH_4^+$;
R is H, $CH_3$, $C_2H_5$, n-$C_3H_7$, or i-$C_3H_7$;
$R^4$ is H, $COCH_3$, or $CH_3$; and
$R^7$, $R^8$, $R^9$ are independently H, $CH_3$, or $CH_3CO$;
or $R^7$ and $R^8$ or $R^8$ and $R^9$ together constitute a carbonyl group (C=O), thus forming a cyclic carbonate;
or $OR^8R^1$ together form a cyclic ester (a lactone); and
≀ indicates that the $OR^9$ substituent can be arranged to afford the R or S absolute configuration:

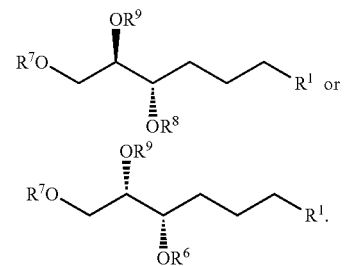

2. The method of claim 1, wherein the compound of formula I has the configuration:

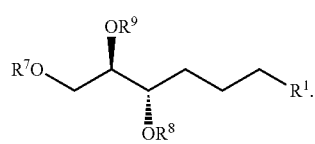

3. The method of claim 1, wherein the compound of formula I has the configuration:

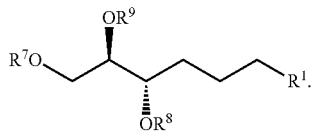

4. The method of claim 2, wherein a compound of formula I is used to treat seasonal or perennial allergic conjunctivitis.

5. The method of claim 2, wherein a compound of formula I is used to treat vernal keratoconjunctivitis, atopic keratoconjunctivitis, or giant papillary conjunctivitis.

6. The method of claim 5, wherein the compound of formula I is used in combination with a histamine receptor antagonist and/or a mast cell stabilizer.

7. The method of claim 6, wherein the histamine receptor antagonist and/or mast cell stabilizer is selected from the group consisting of: emedastine; levocabastine; mequitazine; chlorpheniramine; brompheniramine; astemizole; cetirizine; terfenadine; rocastine; loratadine; desloratadine [that is, 8-chloro-6,11-dihydro-11-(4-piperidinylidene)-5H-benzo[5,6]cyclohepta[1,2-b]pyridine]; 5-[2-[4-bis(4-fluorophenyl)hydroxymethyl-1-piperidinyl]ethyl]-3-methyl-2-oxazolidinone ethanedioate; pyrilamine; clemastine; azelastine; epinastine; ketotifen; olopatadine; mapinastine; lodoxamide; cromolyn sodium; and nedocromil disodium salt.

8. The method of claim 4 or claim 5, wherein the compound of formula I is selected from the group consisting of:

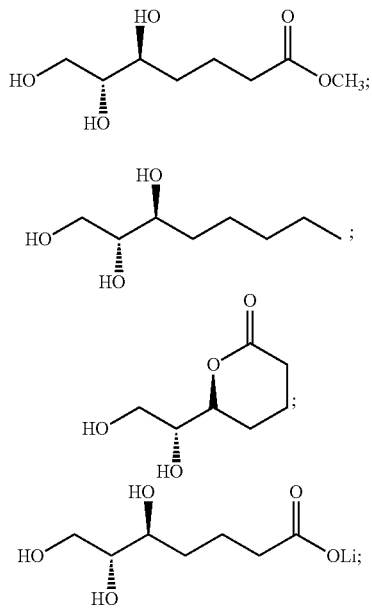

9. The method of claim 7, wherein the compound of formula I is selected from the group consisting of:

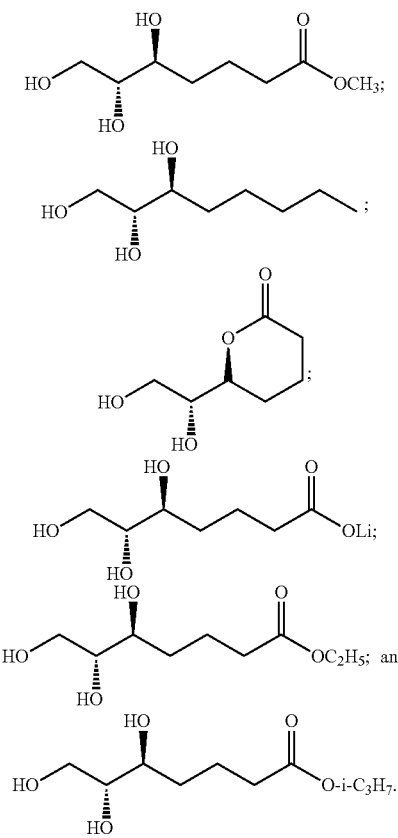

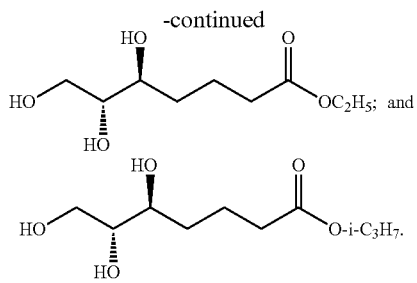

10. The method of claim 1, wherein the pharmaceutically effective amount of the compound of formula I is from 0.00003 to 0.01% (w/v).

11. The method of claim 10, wherein the pharmaceutically acceptable carrier comprises one or more ingredients selected from the group consisting of surfactants; tonicity agents; buffers; preservatives; co-solvents; and viscosity building agents.

* * * * *